United States Patent [19]
Colin et al.

[11] Patent Number: 4,969,747
[45] Date of Patent: Nov. 13, 1990

[54] REVERSE FLOW DISPENSING MIXER

[76] Inventors: Laurence Colin, Box 301, Cross River, N.Y. 10518; Edward R. Spehar, 49 Orion Way, Neshanic Station, 08853; Bernard F. Harkins, 2000 Woodland Ave., S. Plainfield, N.J. 07080

[21] Appl. No.: 470,810

[22] Filed: Jan. 26, 1990

[51] Int. Cl.$^5$ .......................... B01F 5/06; B01F 15/02
[52] U.S. Cl. ...................... 366/339; 366/177; 206/219; 206/384; 222/137; 222/145
[58] Field of Search ............... 366/184, 189, 194, 195, 366/196, 177, 336–340; 222/137, 145; 206/219, 384

[56] References Cited

U.S. PATENT DOCUMENTS

| | | | |
|---|---|---|---|
| 3,286,992 | 11/1966 | Armeiades et al. | 366/339 |
| 3,390,814 | 7/1968 | Creighton, Jr. et al. | 222/137 |
| 4,493,436 | 1/1985 | Brokaw | 222/137 |
| 4,538,920 | 9/1985 | Drake | 366/339 |
| 4,753,536 | 6/1988 | Spehar et al. | 366/189 |
| 4,767,026 | 8/1988 | Keller et al. | 366/393 |
| 4,776,704 | 10/1988 | Kopunek et al. | 366/184 |
| 4,801,008 | 1/1989 | Rich | 206/219 |
| 4,811,549 | 3/1989 | Usami et al. | 222/145 |
| 4,846,373 | 7/1989 | Penn et al. | 222/145 |
| 4,869,400 | 9/1989 | Jacobs | 222/137 |

FOREIGN PATENT DOCUMENTS 0121342 10/1984 European Pat. Off. ............ 366/338

Primary Examiner—Timothy F. Simone

[57] ABSTRACT

A dispensing mixer unit suited for use with a dispensing gun for mixing and dispensing at least two materials through a common mixing nozzle. The dispensing mixer comprises a tubular shell having at least two compartments for separately storing the materials to be intermixed and a common mixing nozzle, with the shell surrounding the common nixing nozzle in a concentric arrangement.

6 Claims, 4 Drawing Sheets

REVERSE FLOW DISPENSING MIXER

FIELD OF THE INVENTION

The present invention is directed to the field of multiple material mixing and dispensing, and more particularly to a dispensing mixer suited for use with a dispensing gun for intermixing and dispensing a composite of materials from a common nozzle.

BACKGROUND OF THE INVENTION

The art of mixing two components, stored separately in a double barrel syringe to form a single mixed product by forcing the components through a static mixing element located in a common discharge nozzle, is described in U.S. Pat. No. 4,753,536, issued to Spehar, et al., on June 28, 1988. The discharge nozzle is removably coupled to the multiple barrel syringe containing the separately stored components to form an elongated dispenser, with the discharge nozzle and multiple barrel syringe axially aligned relative to one another so that the material discharged from the syringe flows along a linear path extending unidirectionally from the syringe through the discharge nozzle. The syringe is, in turn, adapted to be coupled to a pair of plungers from a dispensing gun which has movable pistons for forcing material from each of the barrels upon actuating the plungers. This results in a device which, by necessity, has a relatively long axial dimension, with the length of the syringe, the length of the discharge nozzle, and the length of the gun plunger assembly defining the overall length of the device.

There exist many medical and commercial applications for dispensing a mixed composite product of two or more materials in a very limited working space. In such cases, the space limitation mandates a design configuration in which the length of the device, including the cartridge and mixer, is relatively short.

SUMMARY OF THE INVENTION

The dispensing mixer of the present invention is suited for use with a dispensing gun and includes means for separately storing two or more materials in a tubular shell surrounding a common mixing nozzle in which a static mixing element is placed. In accordance with the design of the present invention, the stored materials are fed in one direction from their respective storage compartments into the common mixing nozzle with the direction of flow then reversed for passage through the mixing nozzle, thereby limiting the overall length of the dispenser. This arrangement condenses the overall length of the unit to less than about fifty percent of the length of the prior art type of dispenser as discussed heretofore.

The dispensing device of the present invention is adapted for mixing and dispensing at least two materials through a common mixing nozzle and comprises:

a tubular shell surrounding said common mixing nozzle with the tubular shell having opposite ends and with said common mixing nozzle extending axially from one of said opposite ends;

partition means located in said shell for dividing said shell into at least two storage compartments for separately storing the materials to be intermixed and dispensed from said device;

piston means axially aligned with said tubular shell and extending from one of said opposite ends in juxtaposition with each of said storage compartments;

a static mixing element disposed in said common mixing nozzle; and means for providing a controlled passageway from each storage compartment in said shell to said common mixing nozzle, such that upon relative advancement of said piston means into said storage compartments, the stored materials are forced to flow in one direction from each storage compartment through said controlled passageway into said common mixing nozzle with the direction of flow reversed through said common mixing nozzle.

BRIEF DESCRIPTION OF THE DRAWINGS

Advantages of the present invention will become apparent from reading the following detailed description of the invention in conjunction with the accompanying drawings of which.

DETAILED DESCRIPTION OF INVENTION

Figure 1:
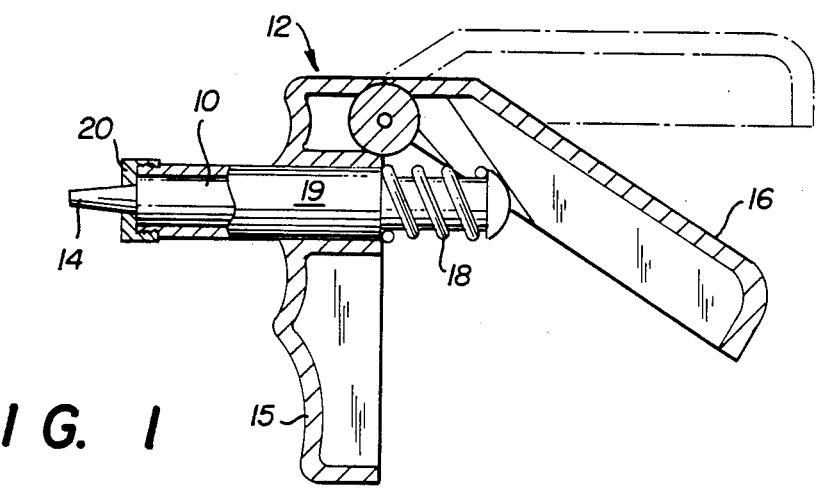
FIG. 1 is a side elevation of a dispensing gun loaded with the dispensing mixer of the present invention for discharging a mixed extruded composite product through a common nozzle.
Figure 2:
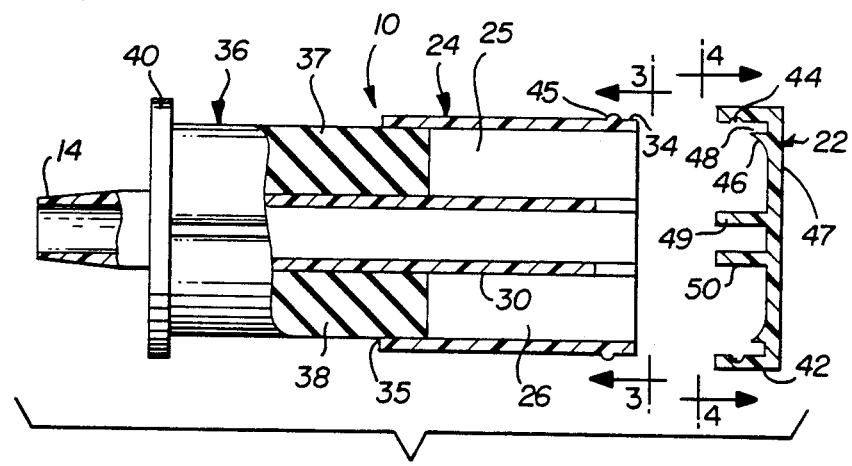
FIG. 2 is a cross-sectional view through the center of the dispensing mixer shown partly in section and partly exploded.
Figure 3:
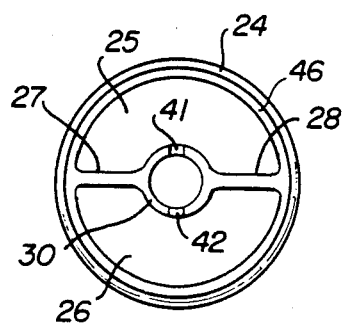
FIG. 3 is an end view of the dispensing mixer of FIG. 2 taken along the lines 3—3 in FIG. 2.

Referring to the drawings, particularly FIG. 1, in which the dispensing mixer (10) of the present invention is shown loaded into a manually-operated extrusion gun (12) for controllably discharging a mixed extruded composite product from a common discharge spout (14) in the dispensing mixer (10). The extrusion gun (12) is, of itself, a conventional extrusion device having a fixed handle (15) which is pistol-shaped and adapted to be gripped by the fingers of one hand, a movable lever (16) which is pivotally connected to the handle (15), and a plunger assembly (18) which engages the lever (16) for slidably moving the plunger (18) into a tubular barrel (19) in response to pressure applied between the handle (15) and the lever (16), preferably using the palm of the same hand holding the gun (12). The dispensing mixer (10) is loaded into the tubular barrel (19) by threadably removing the front tip (20) from the barrel (19). Alternatively, the barrel (19) may be designed with a front end having a semihemispherical geometry (not shown), in substitution for the front tip (20), with the dispensing mixer (10) forced fitted to tightly engage the barrel (19) at such front end. The plunger assembly (18) has a fitting (not shown) in contact with the closure cap (22) for the dispensing unit (10), as shown in FIGS. 2–6. In operation, the plunger (18) presses against the closure cap (22) of the dispensing mixer (10) upon squeezing together the handle (15) and the lever (16). This applies a contraction force between opposite ends of the dispensing mixer (10), which forces the materials stored in the dispensing mixer (10) through the discharge spout (14), as will be discussed hereafter at length.

Referring now to FIGS. 2–9 inclusive, in which the dispensing mixer (10) of the present invention is shown comprising a tubular shell (24) divided into at least two compartments (25) and (26), separated by partition walls (27) and (28), respectively. The partition walls (27) and (28) need not divide the compartments (25) and (26) into equal sizes. The tubular shell (24) surrounds a common mixing nozzle (30) which is preferably of cylindrical geometry. The mixing nozzle (30) is tapered to form a common discharge spout (14). The closure cap (22) is fastened to the rear end (34) of the tubular shell (24) and is rotatable into an open or closed position, as will hereafter be discussed in detail. The compartments (25) and (26) in the tubular shell (24) may be loaded with materials through either opposite end of the tubular shell (24), although preferably from the front end (35) by withdrawing the piston assembly (36) and locking the closure cap (22) on the rear end (34).

The piston assembly (36) includes a plurality of pistons (37) and (38), corresponding in number to the number of storage compartments in the shell (24). The pistons are mounted in sliding engagement over the central mixing nozzle (30), with each piston (37) and (38) juxtaposed in registration, with a corresponding compartment (25) and (26) of the shell (24). The pistons (37) and (38) extend from a common head (40) and are of a geometry and size complementary to the geometry and size of the corresponding compartments (25) and (26) with which each is registered, so that upon applying force to the head (40), the pistons (37) and (38) are driven in common into the compartments (25) and (26), for urging the material contents from the compartments (25) and (26) toward the read end (34) of the tubular shell (24). The compartments (25) and (26) and the corresponding pistons need not be of matching size. Accordingly, any desired ratio may be achieved by using predesigned compartment geometry and volume ratios. The corresponding pistons must match the size of the compartments into which they feed. Thus, the pistons (37) and (38) will apply an equal force to each of the compartments (25) and (26), respectively.

The central mixing nozzle (30) includes slotted openings (41) and (42) adjacent the rear end (34) of the tubular shell (24) which communicate with the storage compartments (25) and (26) to provide for the egress of material from the compartments (25) and (26) upon the application of pressure to the head (40) of the piston assembly (36).

Figure 4:
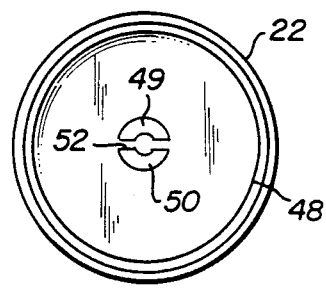
FIG. 4 is an end view of the closure for the dispensing mixer shown in FIG. 2 taken along the lines 4—4 of FIG. 2.
Figure 5:
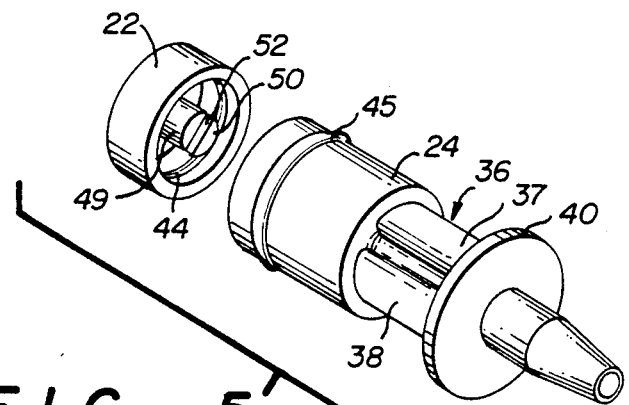
FIG. 5 is a view in perspective of the dispensing mixer of FIG. 2 illustrating how the closure is operatively attached to the shell of the dispensing mixer.
Figure 6:
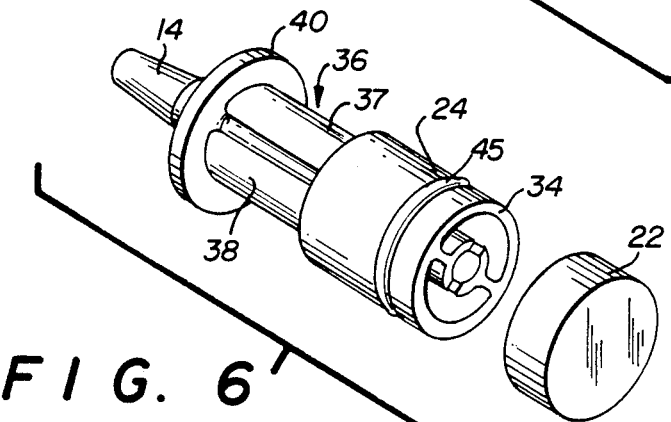
FIG. 6 is another perspective view, similar to FIG. 5, viewed from the side opposite to that of FIG. 5.

The tubular shell (24) has an annular protrusion (45) which locks into an annular slot (44) in the closure cap (22) upon pressing the cap (22) over the rear end (34) of the shell (24). The closure cap (22) has an end wall (47) with a ridge (46) extending from the end wall (47) to form an annular sleeve (48). The ridge (46) is shaped to form a concave curvature facing inwardly to allow a smooth flow of material over the ridge (46). The rear end (34) of the tubular shell (24) slides into the sleeve (48) to form a seal when the cap (22) is fitted over the shell (24). The closure cap (22) also has a pair of curved walls (49) and (50) which extend from the end wall (47) and are complementary to one another. The curved walls (49) and (50) form sectors of a cylinder having a diameter slightly smaller than the diameter of the cylindrical conduit (30), so that when the cap (22) is fitted over the shell (24), the projections (49) and (50) fit within the cylindrical conduit (30) at the rear end (34) of the shell (24) to form a relatively tight fit. The curved walls (49) and (50) are spaced apart, forming a keyway (52), as shown in FIGS. 4 and 5. The alignment of keyway (52) with the openings (41) and (42) in the cylindrical conduit (30) is controlled by manual rotation of the cap (22). In the aligned position, the material from each compartment (25) and (26) will flow into the central mixing nozzle (30) upon applying force to the piston head (40). In the non-aligned position, the openings (41) and (42) are blocked.

A static mixing element (54) (as shown only in FIGS. 7 and 8) is inserted into the hollow mixing nozzle (30) to permit common mixing of the materials in nozzle (30). The interior wall of nozzle (30) may be slightly tapered (not shown) to permit the static mixing element (54) to fit snugly inside. The static mixing element (54) is a conventional device with a multiplicity of twisted, auger-like mixing blades. The number of mixing blades (51) controls how well the materials intermix to form a homogeneously mixed product within the nozzle (30).

Figure 7:
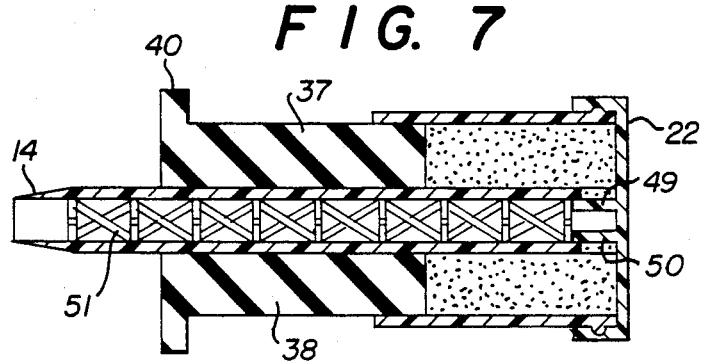
FIG. 7 is a view in longitudinal cross section of the dispensing mixer of FIG. 2 shown in its fully extended position with the storage compartments shown completely filled and before operating the unit.
Figure 8:
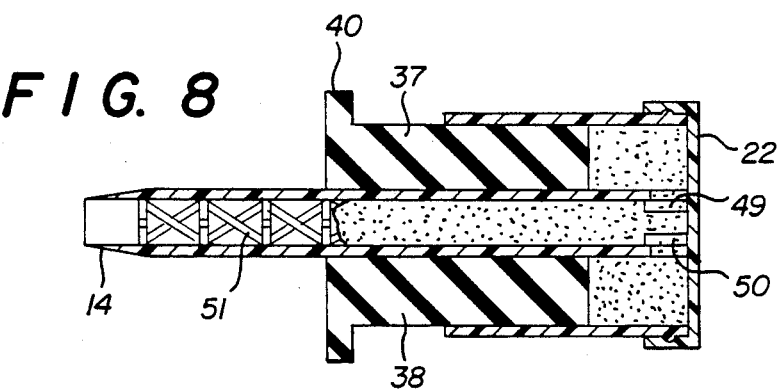
FIG. 8 is another view, similar to FIG. 7, with the dispensing mixer of the present invention partially actuated so that storage material has begun to intermix through the mixing nozzle.
Figure 9:
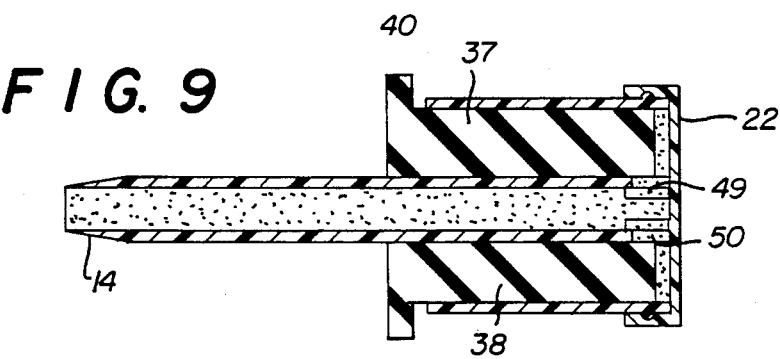
FIG. 9 is yet another view, similar to FIG. 8, with the dispensing mixer of the present invention shown substantially fully discharged.

The dispensing mixer (10) is ready to be inserted into the extrusion gun (12) of FIG. 1 once the compartments (25) and (26) are loaded with a desired material, and the cap (22) rotated to align the slot (52) with the openings (41) and (42), as shown in FIG. 7. Any material composition of any desired viscosity may be loaded into the compartments (25) and (26) of the tubular shell (24). Resin materials, which upon intermixing become active for use as an adhesive or as a dental filling material, are particularly well suited for use in the mixer (10). It should, however, be understood that any materials which require intermixing in situ immediately before use, particularly materials having a heavy consistency, may be used. FIGS. 8 and 9 show the dispensing mixer in a partially discharged and a substantially fully discharged position, respectively. At any interim discharge position, the mixer (10) may be removed from the gun (12) and the cap (22) rotated to temporarily block further egress of material through the discharge nozzle (32). Once the materials are mixed, the dispensing mixer is reusable only upon removal and replacement of the static mixing element (54) before the mixed materials in the common mixing nozzle (30) gel.

Figure 10:
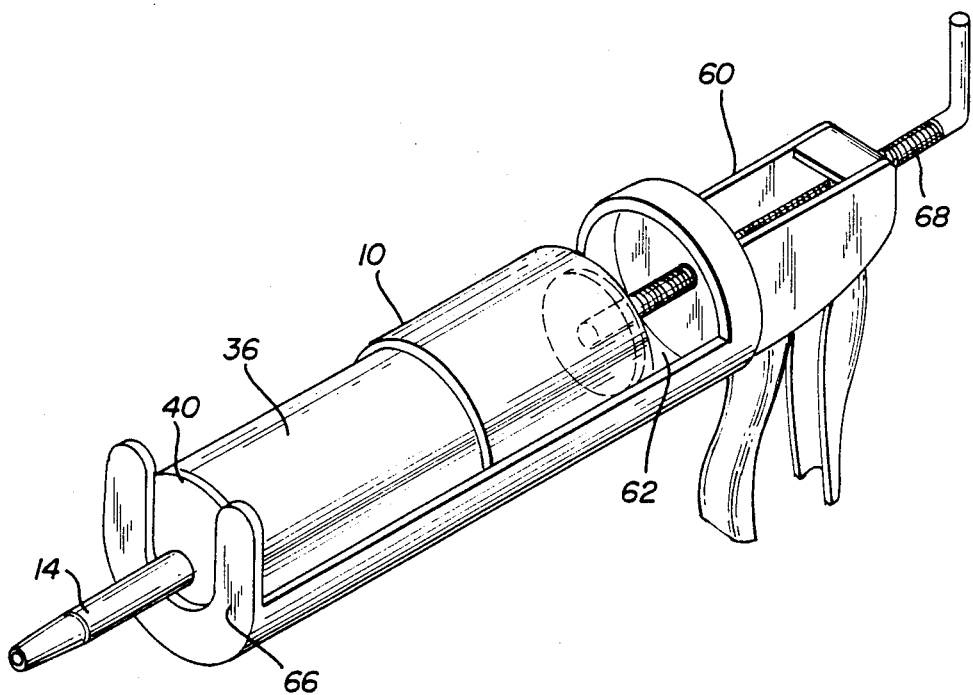
FIG. 10 shows the dispensing mixer of the present invention loaded into another type of conventional cartridge gun for dispensing a mixed extruded composite product.

A conventional-type caulking gun (60) may also be used to operate the dispensing mixer (10), as shown in FIG. 10. The dispensing mixer (10) would be loaded into the open breach (62) of the caulking gun (60). To receive the mixer (10), the end face (66) of the gun (60) has a horseshoe-like configuration which engages the head (40) of the piston assembly (36). Upon actuating the conventional pawl and ratchet hand-control mechanism (68), a constricting force is developed between the head (40) and the closure cap (22) of the mixer (10), for discharging mixed effluent from the discharge spout (14), as explained heretofore in connection with FIG. 1.

What we claim is:

1. A dispensing mixer for intermixing and dispensing at least two materials through a common mixing nozzle comprising:
    a tubular shell surrounding said common mixing nozzle with said tubular shell having opposite ends and with said nozzle extending axially from one of said opposite ends;
    partition means located in said shell for dividing said shell into at least two storage compartments for separately storing the materials to be intermixed and dispensed from said device;
    piston means axially aligned with said tubular shell and extending from one of said opposite ends in juxtaposition with each of said storage compartments;
    a static mixing element disposed in said common mixing nozzle; and
    means for providing a controlled passageway from each storage compartment in said shell to said common mixing nozzle, such that upon relative advancement of said piston means into storage compartments, the stored materials are forced to flow in one direction from each storage compartment through said controlled passageway into said common mixing nozzle with the direction of flow reversed through said common mixing nozzle.

2. A dispensing mixer, as defined in claim 1, wherein said means for providing a controlled passageway comprises an opening in said mixing nozzle for communicating with each compartment.

3. A dispensing mixer, as defined in claim 2, further comprising closure means for sealing the end of said tubular shell opposite said piston means.

4. A dispensing mixer, as defined in claim 3, wherein said closure means further comprises control means for opening said controlled passageway in one position of said closure means and for blocking said controlled passageway in another position.

5. A dispensing mixer, as defined in claim 4, wherein said closure means includes a keyway for opening or closing said controlled passageway upon manual rotation of said closure means.

6. A dispensing mixer, as defined in claim 2, wherein said piston means comprises a piston head and a fixed number of pistons extending from the head, corresponding to the number of storage compartments.

* * * * *